(12) United States Patent
Sridharan et al.

(10) Patent No.: US 12,082,628 B2
(45) Date of Patent: Sep. 10, 2024

(54) BRASSIERE FOR USE IN MAMMOGRAPHY IMAGING PROCEDURES

(71) Applicant: GE Precision Healthcare LLC, Wauwatosa, WI (US)

(72) Inventors: Pradeep Kumar Sridharan, Bangalore (IN); Authavan Revathy Muthu, Bangalore (IN)

(73) Assignee: GE Precision Healthcare LLC, Wauwatosa, WI (US)

( * ) Notice: Subject to any disclaimer, the term of this patent is extended or adjusted under 35 U.S.C. 154(b) by 49 days.

(21) Appl. No.: 17/966,266

(22) Filed: Oct. 14, 2022

(65) Prior Publication Data

US 2024/0122274 A1    Apr. 18, 2024

(51) Int. Cl.
*A41C 3/00*    (2006.01)
*A61B 6/50*    (2024.01)

(52) U.S. Cl.
CPC ............ *A41C 3/0064* (2013.01); *A61B 6/502* (2013.01)

(58) Field of Classification Search
CPC ............................ A41C 3/0064; A61B 6/502
USPC .......................................................... 450/38
See application file for complete search history.

(56) References Cited

U.S. PATENT DOCUMENTS

| | | | | |
|---|---|---|---|---|
| 5,347,656 A | * | 9/1994 | Fabritz | A41C 3/105 450/38 |
| 5,697,974 A | * | 12/1997 | Wang | A41C 3/105 623/7 |
| 5,782,671 A | * | 7/1998 | Suen | A41C 3/10 450/38 |
| 5,833,515 A | * | 11/1998 | Shahbazian | A41C 3/105 450/38 |
| 8,858,295 B2 | | 10/2014 | Thompson | |
| 9,301,559 B2 | * | 4/2016 | McQueer | A41D 13/05 |
| 11,000,241 B2 | | 5/2021 | St. Pierre et al. | |
| 2005/0245850 A1 | | 11/2005 | Freyre et al. | |
| 2017/0231291 A1 | * | 8/2017 | Lima | A41C 3/105 450/38 |
| 2019/0240109 A1 | * | 8/2019 | Barkay | A41C 3/0064 |
| 2021/0015435 A1 | | 1/2021 | Defreitas et al. | |

FOREIGN PATENT DOCUMENTS

JP        4392225 B2      12/2009

* cited by examiner

*Primary Examiner* — Gloria M Hale
(74) *Attorney, Agent, or Firm* — Boyle Fredrickson S.C.

(57) ABSTRACT

According to one aspect of an exemplary embodiment of the disclosure, a mammography imaging system or device includes a brassiere including one or more inflation chambers to assist in automatically positioning the breast. The brassiere includes cup in which the breast is positioned that includes a radiolucent cushion material along with the chambers and one or more inflatable chambers to compress/push the breast forward to position the breast within the cup as desired. In addition, the brassiere includes a vacuum system secured to the front part of the cup to pull the tip or nipple portion of the breast forward with vacuum-based suction technique. With the initial compression of the breast within the cup, the compression paddle of the imaging system can then be employed to apply any necessary additional force across the breast to achieve the required breast position and thickness for the selected image view, with the cushion material limiting any discomfort from the compression.

20 Claims, 12 Drawing Sheets

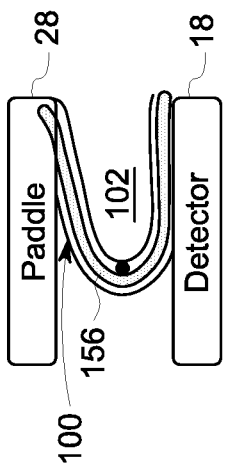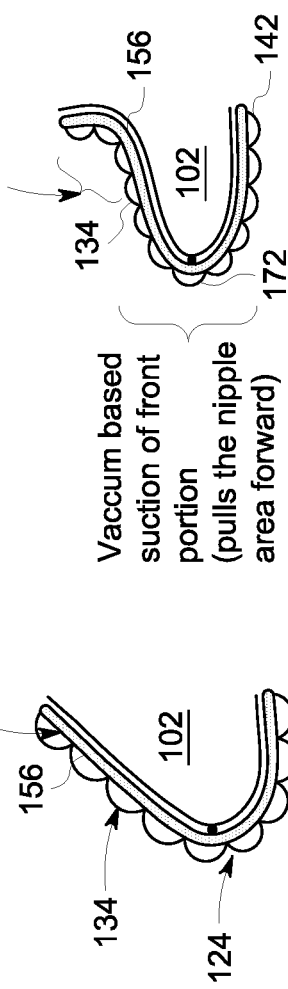

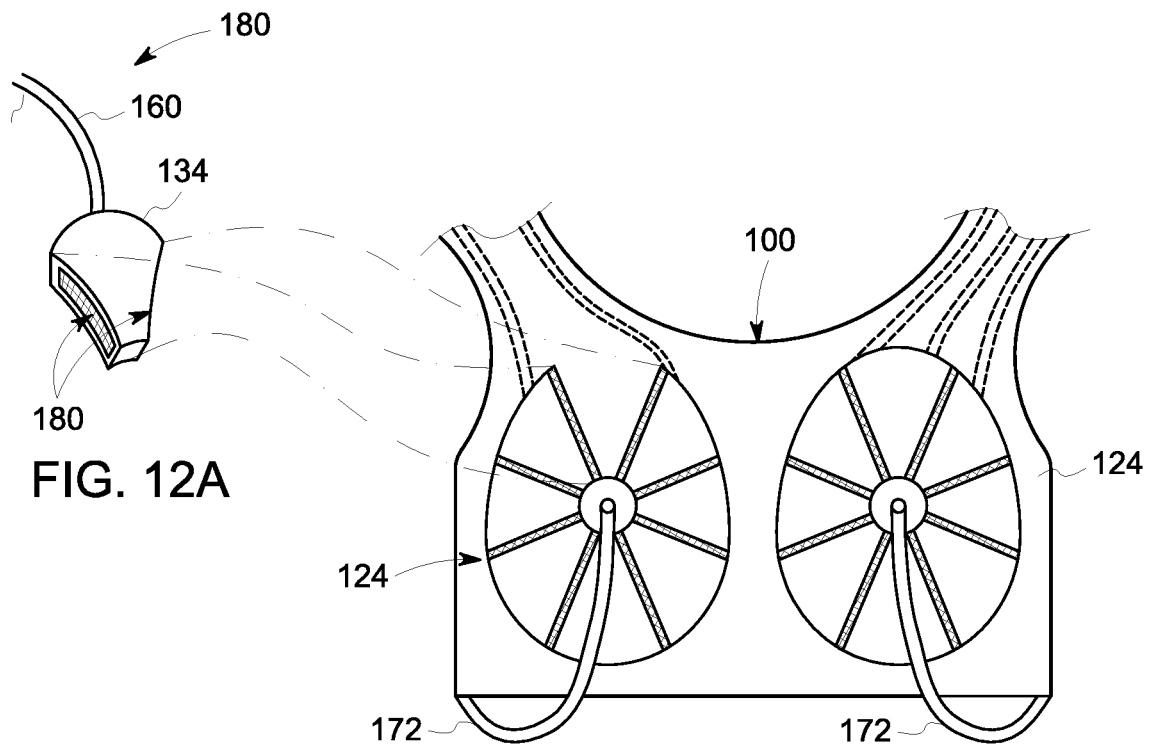
FIG. 12A
FIG. 12B
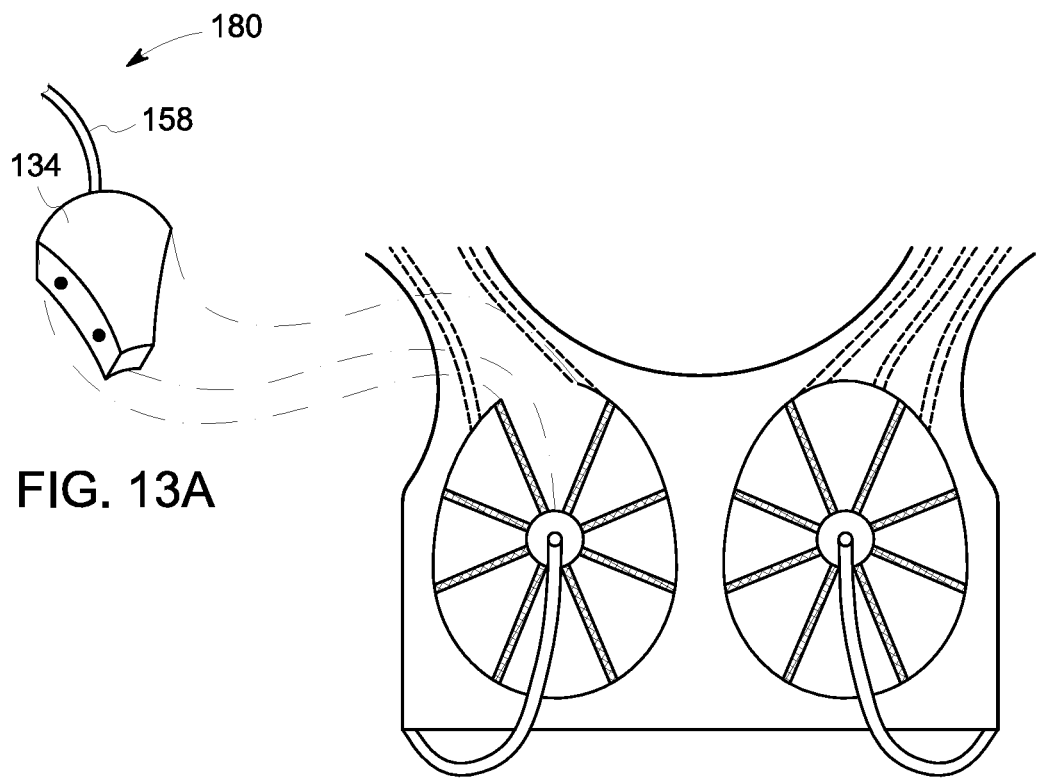
FIG. 13A
FIG. 13B

BRASSIERE FOR USE IN MAMMOGRAPHY IMAGING PROCEDURES

FIELD OF THE DISCLOSURE

The present disclosure relates generally to medical imaging systems, including mammography systems and devices, and more specifically to a brassiere utilized in mammography procedures to increase patient comfort during the imaging procedure.

BACKGROUND OF THE DISCLOSURE

Embodiments of the invention relate generally to X-ray medical imaging, and more particularly to devices, systems and methods employed to perform various imaging procedures, such as mammography imaging procedures including but not limited to spectral mammography (SM), such as 2D/3D dual-energy contrast-enhanced (CE) mammography exams, or digital breast tomosynthesis (DBT) mammography exams.

Even though women are aware of the significant benefits of an annual mammogram for the detection of breast cancer, many are reluctant to have the procedure performed due to the fear of pain, discomfort and radiation often associated with mammograms. It has recently been noted that nearly 1 in 6 women report that pain and discomfort, e.g., contact with the cold breast compression surfaces, has deterred them from getting a mammogram as recommended. Further, a significant number of women reported postponing a mammogram due to the discomfort during the procedure, and still others said they would not get any further mammograms performed because of the high level of discomfort.

In addition to the discomfort associated with mammography procedures, whether actual or perceived, the radiation dose to the patient is also of concern. On many occasions, the initial procedure results in images that are deficient for a number of reasons, such that the procedure must be performed again to retake the images. As the radiation dose to the patient increases with the number of retakes, patients do not want to be exposed to any more than the minimum radiation dose necessary to obtain the required images for diagnostic purposes. However, as per a study performed by the American College of Radiology (ACR), of all of the clinical images analyzed in the study which were deemed deficient on the first attempt and led to a re-take, 92% of those images were a direct result of poor breast positioning prior to obtaining the images and mainly due to technologist training and/or experience. As a result, in addition to the discomfort of the mammography procedure, issues with regard to breast positioning are also significant in the perception of the mammography procedure.

In order to address these issues, a number of prior art solutions have been developed. Referring to FIGS. 1A-1B, one prior art solution is the use of flexing or pivoting compression paddles. The compression paddle is a rigid structure formed of a radiolucent material to enable x-rays to pass unhindered through the paddle. Normally the paddle is disposed parallel to the surface of the detector on which the breast is positioned prior to the mammography imaging procedure. The paddle is moved downwardly into contact with the breast to compress the breast between the paddle and the detector, to both reduce the thickness of the breast and improve image quality and to retain the breast in a stationary position during the imaging process.

To alleviate some of the discomfort created by the parallel paddle configuration (FIG. 1A), the flex paddle in FIG. 1B is secured to a support mechanism using a pivot that enables the paddle to pivot with regard to the support structure, resulting in a more comfortable configuration for the paddle on the breast, i.e., to adjust their position to the conic shape of the breast and enable the compressed breast thickness to decrease in a quasi-linear fashion from the chest wall to the nipple.

Another prior art accommodation to attempt to address the pain and discomfort associated with mammography procedures is the use of a breast cushion. As shown in FIG. 2, the cushion is positioned on the detector surface, such that the cushion pad provides a softer surface on the detector against which the breast is compressed by the compression paddle, of the compressed breast, lessening the discomfort of compression of the breast. Further, the material forming the cushion pad also operates to grip the breast to assist in holding the breast in the stationary position during compression and during the imaging procedure.

Still another attempt to improve the comfort and perception of the mammography procedure for a patient involves providing the patient with the control of the movement of the compression paddle such as disclosed in US Patent Application Publication No. US20200060632, entitled Apparatus And Method For Mammographic Breast Compression, which is hereby expressly incorporated by reference herein in its entirety for all purposes. The patient holds a control device that operates the support structure for the compression paddle, such that the patient can move the paddle to compress the breast between the paddle and the detector. While the paddle is still moved into the position where the breast is compressed to the required degree for optimal imaging of the breast, the control of the movement by the patient affords the patient with a significant increase in the perceived comfort of the mammography imaging procedure.

However, each of the aforementioned prior art attempts at reducing actual or perceived discomfort in a mammography imaging procedure have certain shortcomings. In particular, the flex paddles and the pad and patient control mainly address the physiologic factors concerning discomfort for the patients, as there is still appreciable pain observed with the flex paddles, the cushion pad, and the patient control due to the need for compression of the breast to the required level for imaging of the breast.

Therefore, it is desirable to develop an improved device, system and method for more adequately addressing the psychological, physiological, and sociologic factors associated with mammography imaging procedures in order to provide increased comfort to the patient being imaged.

SUMMARY OF THE DISCLOSURE

According to one aspect of an exemplary embodiment of the disclosure, a brassiere for use in conjunction with a mammography imaging device including a body including at least one aperture formed therein, a cup secured to the body around the aperture, the cup including at least one inflatable chamber and at least one cushion disposed on a breast contact surface of the cup and an inflation module operably connected to the at least one inflatable chamber to selectively inflate and deflate the at least one inflatable chamber.

According to still another aspect of an exemplary embodiment of the present disclosure, a mammography system including a gantry including radiation source, a detector alignable with the radiation source, and a compression paddle moveable relative to the detector to secure a patient breast therebetween, a controller operably connected to the gantry to control the operation of the radiation source and detector to generate image data, and to control the operation of the biopsy device in an interventional/biopsy mode for the mammography system, the controller including a central processing unit and interconnected database for processing the image data from the detector, a display operably connected to the controller for presenting information to a user, and a user interface operably connected to the controller to enable user input to the controller and a brassiere adapted to compress a breast into a desired position prior to placement of the breast on the detector, the brassier including a body including at least one aperture formed therein, a cup secured to the body around the aperture, the cup including at least one inflatable chamber and at least one cushion disposed on a breast contact surface of the cup and an inflation module operably connected to the at least one inflatable chamber to selectively inflate and deflate the at least one inflatable chamber.

According to still another aspect of an exemplary embodiment of the present disclosure, a method for compressing a breast into a desired shape for a mammography imaging procedure on an imaging device includes the steps of providing a brassiere having a body including at least one aperture formed therein, a cup secured to the body around the aperture, the cup including at least one inflatable chamber and at least one cushion disposed on a breast contact surface of the cup and an inflation module operably connected to the at least one inflatable chamber to selectively inflate and deflate the at least one inflatable chamber, positioning the breast within the cup, and inflating the at least one inflatable chamber to compress the breast.

These and other exemplary aspects, features and advantages of the invention will be made apparent from the following detailed description taken together with the drawing figures.

BRIEF DESCRIPTION OF THE DRAWINGS

The drawings illustrate the best mode currently contemplated of practicing the present invention.

In the drawings:

FIGS. 10A-10C are schematic views of the compression steps of the method of FIG. 9 in accordance with an embodiment of the disclosure.

FIGS. 12A and 12B are isometric views of another embodiment of the brassiere of FIG. 5 and a separable inflation chamber, in accordance with an embodiment of the invention.

FIGS. 13A and 13B are isometric views of another embodiment of the brassiere of FIG. 5 and a separable inflation chamber, in accordance with an embodiment of the invention.

DETAILED DESCRIPTION OF THE DRAWINGS

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

As used herein, "electrically coupled", "electrically connected", and "electrical communication" mean that the referenced elements are directly or indirectly connected such that an electrical current may flow from one to the other. The connection may include a direct conductive connection, i.e., without an intervening capacitive, inductive or active element, an inductive connection, a capacitive connection, and/or any other suitable electrical connection. Intervening components may be present.

Further, while the embodiments disclosed herein are described with respect to a mammography apparatus for the 2-dimensional imaging of breast tissue, it is to be understood that embodiments of the invention may be applicable to other types of imaging devices for both 2-dimensional and 3-dimensional imaging including, for example, digital breast tomosynthesis (DBT) and spectral mammography (single or multi-energy), as well as for imaging procedures for tissue other than breast tissue. Further still, embodiments of the invention may be used to analyze tissue, generally, and are not limited to analyzing human tissue.

Figure 2:
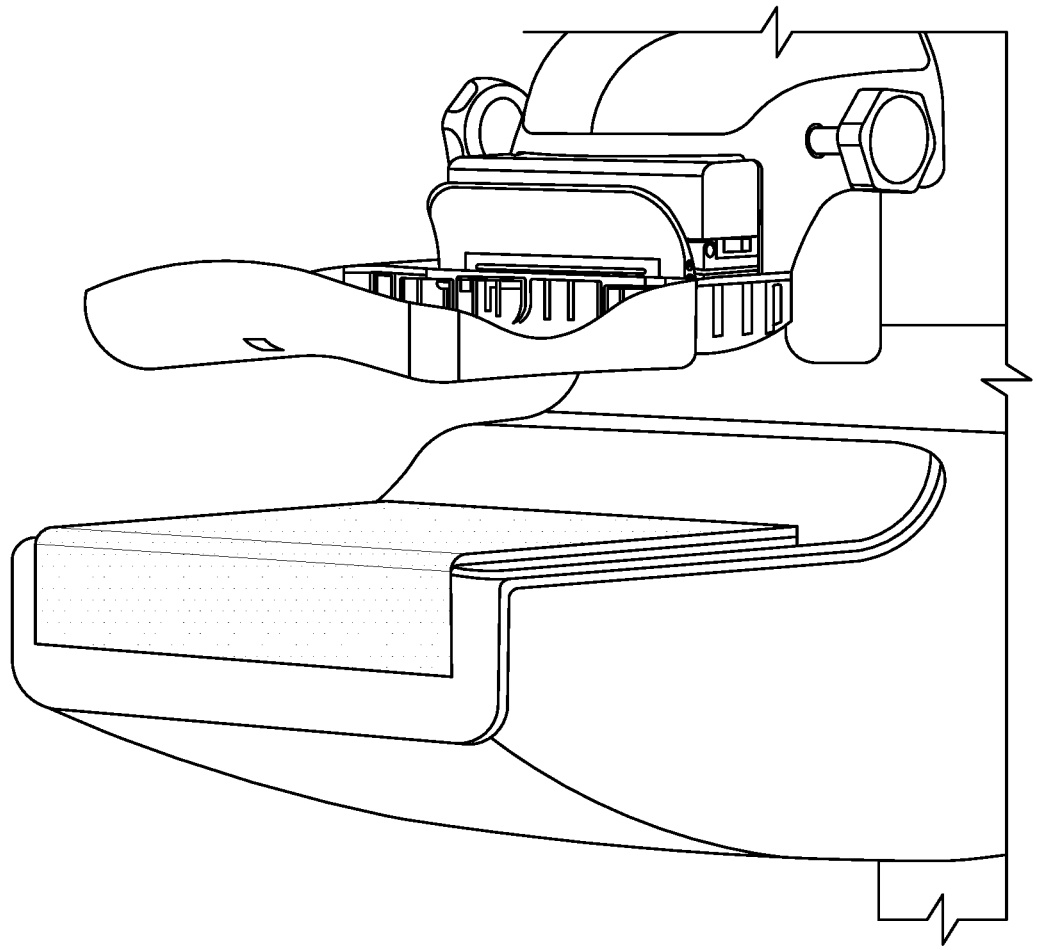
FIG. 2 is an isometric view of a prior art mammography detector cushion disposed on a detector of a mammography device.
Figure 3:
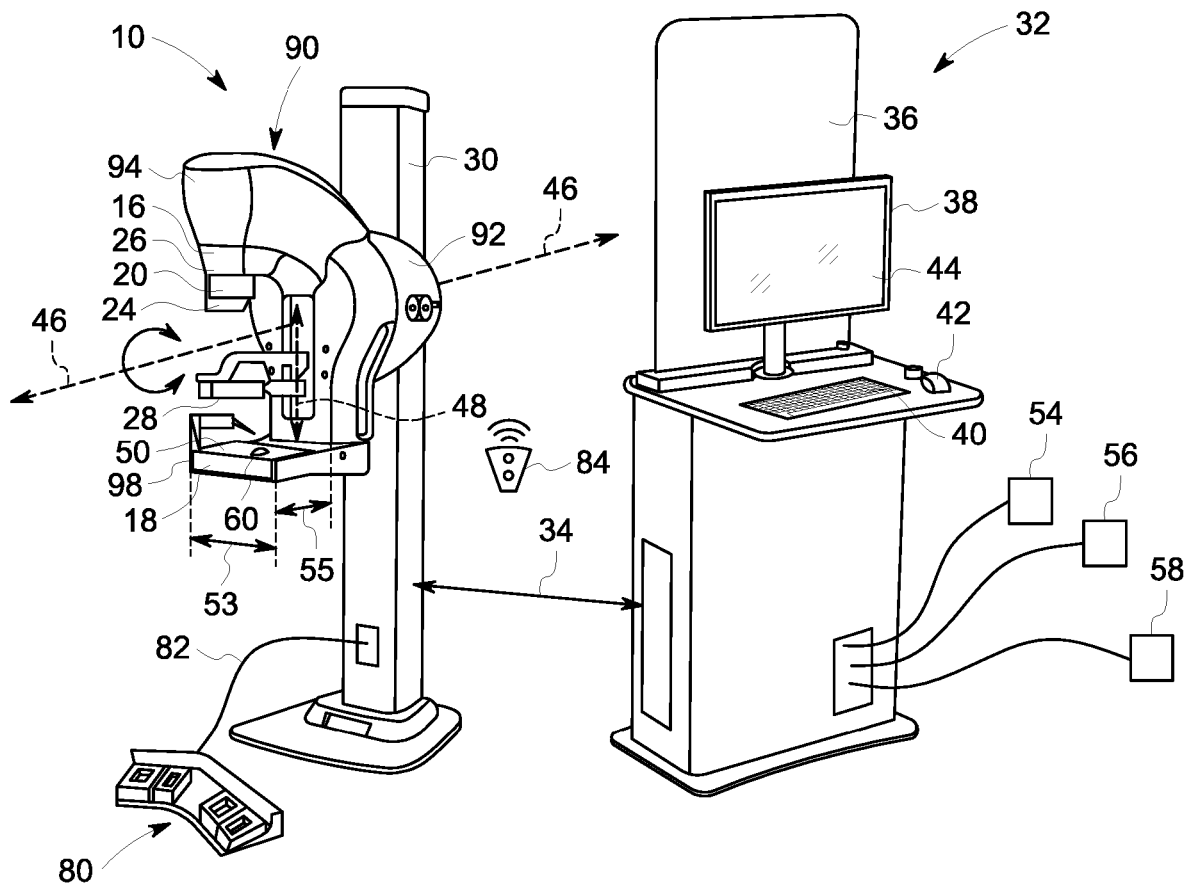
FIG. 3 is a perspective view of an imaging device in the form of a mammography imaging system for imaging the breast tissue of a patient, in accordance with an embodiment of the disclosure.
Figure 4:
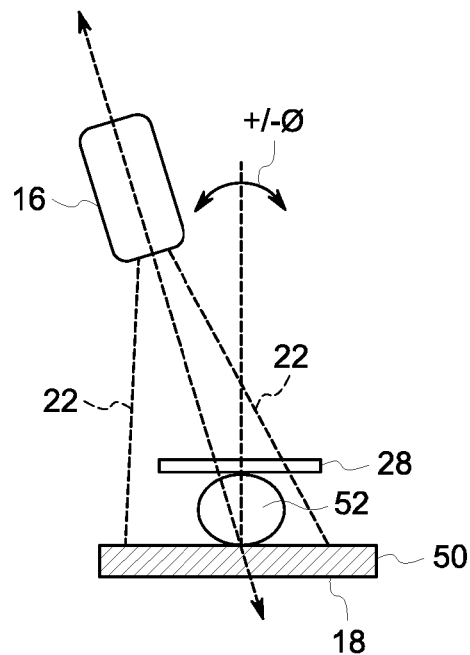
FIG. 4 is a diagram of the system of FIG. 3, showing the radiation source of the system in a scanning position, in accordance with an embodiment of the disclosure.

Referring now to FIGS. 3 and 4, the major components of an exemplary imaging system 10 formed as a mammography system 12 for imaging breast tissue according to an embodiment of the invention are shown. The system 10, such that disclosed in US Patent Application Publication No. US20200060632, entitled Apparatus And Method For Mammographic Breast Compression, the entirety of which is expressly incorporated herein by reference for all purposes, includes a radiation source/x-ray source 16, a radiation detector 18, and a collimator 20. The radiation source 16 is movable between a variety of imaging positions relative to the detector 18, and is operative to emit radiation rays 22 (FIG. 2) that are received by the radiation detector 18 to provide an image of a breast 52. In embodiments, the system 10 may include a patient shield 24 mounted to the radiation source 16 via face shield rails 26 to prevent the patient's head from obstructing the radiation rays and protecting the patient from the radiation rays 22.

Figure 1A:
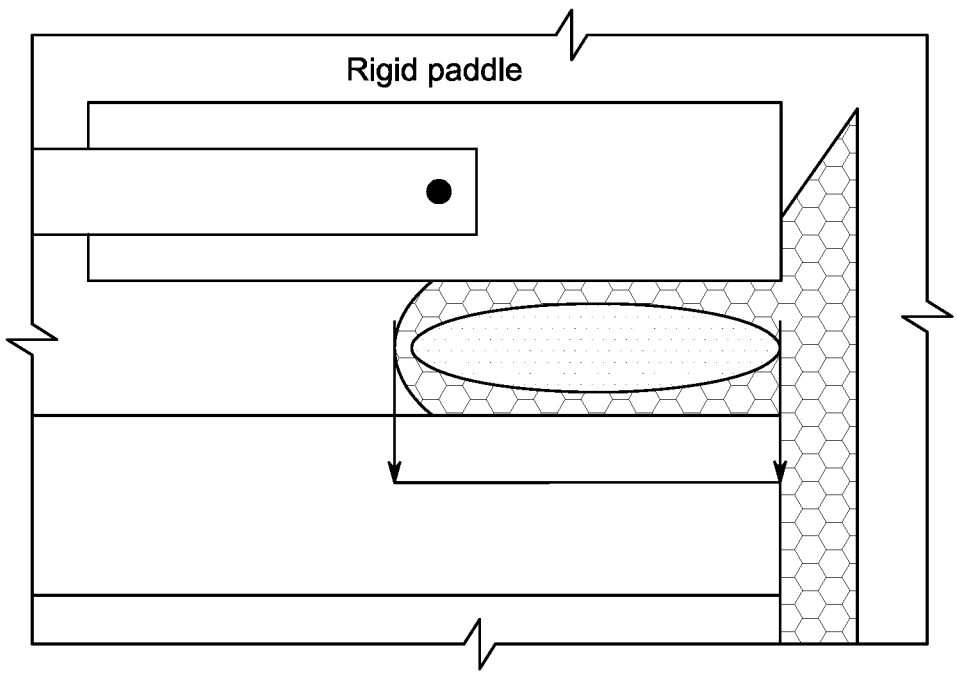
FIGS. 1A and 1B are perspective views of prior art compression paddle utilized with a mammography imaging device.
Figure 1B:
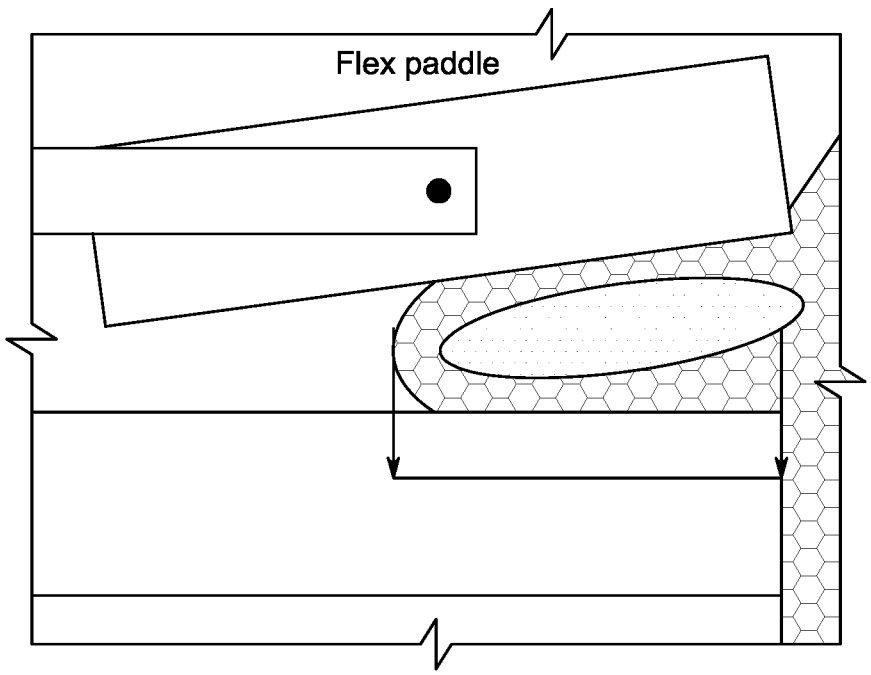

Referring still further to FIGS. 3 and 4, the system 10 also includes a compression paddle or plate 28 and a support structure 30 to which one or more of the radiation source 16, radiation detector 18, and/or compression plate 28 may be mounted to. In embodiments, the system 10 may further include a controller 32. The controller 32 may be a workstation having at least one processor/central processing unit/computer and a memory device/database that stores information and/or instructions for the operation of the system 10 that are employed by the controller 32, as shown in FIG. 1 or, in other embodiments, the controller 32 may be embedded/integrated into one or more of the various components of the system 10 disclosed above. In embodiments, the controller 32 may be in electrical communication with the radiation source 16, radiation detector 18, and/or the compression plate 28 via a cable 34. As will be appreciated, in embodiments, the connection 34 may be a wireless connection. In embodiments, the controller 32 may include a radiation shield 36 that protects an operator of the system 10 from the radiation rays 22 emitted by the radiation source 16. The controller 32 may further include a display 38, a keyboard 40, mouse 42, and/or other appropriate user input devices that facilitate control of the system 10 via a user interface 44.

As further shown in FIGS. 3 and 4, the radiation source 16, along with the radiation detector 18, forms part of an x-ray system which provides x-ray imagery for the purpose of imaging a body part of a patient, such as breast 52. As stated above, the radiation source 16 emits the radiation rays 22 such that the radiation rays 22 travel from the radiation source 16 to the radiation detector 18. While the radiation rays 22 are discussed herein as being x-rays, it is to be understood that the radiation source 16 may emit other types of electromagnetic rays which can be used to image a patient. The radiation source 16 may be mounted to the support structure 30 such that the radiation source can rotate around an axis 46 in relation to the radiation detector 18, although movement of the radiation source 16 in paths other than rotation about a fixed axis, such as during digital breast tomosynthesis (DBT), are also envisioned. In embodiments, the radiation detector 18 may be configured to rotate or translate within its housing, such as in the directions indicated by arrows 53 and 55.

In the illustrated exemplary embodiment of FIG. 3 the radiation source 16 and the detector 18 are mounted to a gantry 90 that is secured to the support structure 30. The support structure 30 houses a translation mechanism 92 that is operably connected to the gantry 90. The translation mechanism 92 is operable to move the gantry 90 vertically with respect to the support structure 30 in order to position the gantry 90 at the appropriate height to accommodate the dimensions of the patient on which the system 10 is being utilized. The translation mechanism 92 is also operable to rotate the gantry 90 relative to the support structure 30 about the horizontal axis 46 in order to position the gantry 90 rotationally with regard to the patient, as necessary.

The gantry 90 includes a generally C-shaped body 94 with the radiation source 16 at one end and the detector 18 at the opposite end. In this configuration, regardless of the vertical and/or rotational orientation of the gantry 90, such as to position the radiation source 16 and detector 18 relative to the patient breast 52 to obtain x-ray images at various orientations, such as for craniocaudal (CC) or mediolateral oblique (MLO) views, among others, the radiation source 16 is disposed in alignment with the detector 18. In this position, the detector 18 is capable of receiving the x-rays 22 emitted from the radiation source 16 that pass through the portion of the patient, i.e., patient breast 52, located between the radiation source 16 and the detector 18 in order to generate image data for transmission to the control system 32 of the mammography device/system 10 to create/reconstruct a 3D image dataset for viewing by a physician, such as by using DBT, among other known methods.

Additionally, in another embodiment the radiation source 16 can be attached to the gantry 90 to rotate and/or move independently of the gantry 90 and detector 18 in order to enable the radiation source 16 to take x-ray images of the patient breast at various angles relative to the detector 18, e.g., between +/−60°. The images obtained between these angles for the radiation source 16 can be used either for creation of stereoscopic images in a biopsy procedure using the system 10 or for DBT when operating the system 10 in an imaging mode.

As stated above, the radiation detector 18 receives the radiation rays 22 emitted by the radiation source 16. In embodiments, data regarding the radiation rays 22 received by the radiation detector 18 may be electrically communicated to the controller 32 from the radiation detector 18 via cable/electronic connection 34 such that the controller 32 generates one or more images which may be shown on the display 38 and stored in the memory device.

The compression plate 28 is operative, in response to instruction from the controller 32 or in response to instructions from controller(s) on or near the mammography system 10 or switch controllers 80, to move towards and away from the radiation detector 18 as indicated by arrows 48 such that the compression plate 28 flattens and holds a body part, e.g., breast 52, in place against the surface 50 of the radiation detector 18. In this respect, the radiation detector 18 and the surface 50 thereof is referred to herein as a "support plate" that cooperates with the compression plate 28 to compress and clamp a breast of a patient therebetween.

In one exemplary embodiment, in order to maintain the position of the patient breast 52 stationary during the imaging and/or biopsy procedures, the compression plate 28 is attached to a plate or paddle support mechanism 45 located on and/or within the gantry 90 that positions the compression plate 28 directly over and in alignment with the detector 18/support plate and operably connected to the controller 32. The plate support mechanism 45 is operable within the gantry 90 at any rotational or vertical position of the gantry 90 to move the plate 28 in a line either towards or away from the detector 18/support plate. The mechanism 45 can have any of a number of different configurations, but in one exemplary embodiment takes the form of a compression screw mechanism that is operable to move the plate 28 into engagement with the patient breast 52 to exert a predetermined pressure/compression on the breast 52 to retain the breast 52 in a stationary position between the plate 28 and the detector 18/support plate during imaging and/or biopsy procedures.

In operation, as best shown in FIG. 4, in accordance with an embodiment, the breast 52 of the patient may be placed onto the surface 50 of the radiation detector 18. The compression plate 28, under control of the plate support mechanism 45 by the controller 32, moves towards the detector 18 to compress the breast 52 against the surface 50 of the detector 18 such that the breast 52 is immobilized. Movement of the compression plate 28 towards the detector 18 to compress the breast 52 against the support plate/detector 18 defines a compression phase of the system 10. Once a target compression is achieved, movement of the compression plate 28 is halted and the compression plate 28 and the support plate 18 are held in fixed position to clamp the breast 52 therebetween (referred to herein as the clamping phase) so that imaging or procedures, e.g., a biopsy, may be commenced. During an imaging procedure, the radiation source 16 is selectively adjusted such that it is moved/rotated to a first scanning position and scans the breast 52. The radiation detector 18 receives the radiation rays 22 passing through the breast 52 and sends data to the controller 32 which then generates one or more x-ray images of the breast 52. Once imaging is complete, the controller 32 moves the compression plate 28 away from the support plate 18 to free the breast 52. Additionally, the system 10 can include a biopsy system 98 that can be operated to perform a biopsy procedure on the compressed breast 52 on the system 10 after obtaining one or more images of the breast 52.

Referring still further to FIG. 3, in an embodiment, the system 10 may include one or more physiological monitoring or sensor devices 54, 56, 58, 60 communicatively coupled with the controller 32 for monitoring one or more physiological parameters of a patient (and for transmitting physiological parameter data to the controller 32). While FIG. 3 illustrates that the sensor devices 54, 56, 58 are connected to the controller 32, in some embodiments, one or more of the sensor devices may be communicatively coupled with the mammography apparatus, without departing from the broader aspects of the invention. The sensor devices may be selected to monitor and/or measure any physiological information of a patient desired, including, but not limited to, diastolic blood pressure, systolic blood pressure, body temperature, blood oxygen level, patient weight, skin conductance, pulse rate, etc. As illustrated in FIG. 3, one or more of the sensor devices, e.g., sensor device 60, may be physically integrated with the compression plate 28 and/or the detector/support plate 18. By incorporating the sensor devices into the support plate 18 or compression plate 28, physiological parameter data of the patient may be acquired and transmitted to the controller 32 without requiring any additional intervention by the system operator.

In an embodiment, the sensor device 60 may be a force sensor for measuring the amount of pressure or compressive force applied to the breast 52. Additional sensors for measuring physiological parameters may be configured to either directly measure or allow the calculation of variables such as force, pressure, temperature, rigidity, elasticity, breast size and/or volume, and/or tissue density and could be embedded in compression plate 28 or support plate 18 or attached as part of mammography system 10.

The various sensor devices 54, 56, 58, 60 may be configured to acquire physiological parameter data and/or other sensor data from a patient during system operation. More specifically, physiological parameter data may be acquired continuously or at predetermined time intervals before breast compression and imaging, during the compression phase of the system and/or during the clamping phase of the system. In an embodiment, the physiological parameter data may be acquired continuously or at predetermined time intervals during at least the compression phase. In other embodiments, the physiological parameter data may be acquired continuously or at predetermined time intervals during at least the compression phase and the clamping phase.

Referring once again to FIG. 3, in an embodiment, operation of the system 10 during the compression phase and the clamping phase may be controlled by the patient using switch controls 80, e.g., footswitch controls, such as disclosed in U.S. Pat. No. 10,004,470, which is hereby incorporated by reference herein in its entirety. Switch controls 80 are typically connected via a cable/wire 82 to mammography imaging system 10. The controls are also often mirrored on the opposite side of mammography imaging system 10 (not shown). Other controls (not shown) may be present on particular accessories placed either in the paddle/breast support area. In an embodiment, rather than being footswitch controls, the switch controls may be a handheld control unit 84 with a wired, wireless, Bluetooth or other connection with the system 10. In an embodiment, the patient may control the rate of compression and/or pressure or force applied during the compression phase and/or clamping phase using the switch controls. A feedback device, e.g. controller 32, may be configured to give feedback information about the image to obtain and may designed such that the feedback information is operatively perceivable by the patient (e.g., through an audible or visual indication). The feedback device, e.g., controller 32, may be configured to provide feedback information to the patient regarding the rate of compression (greater or lower rate of compression) and/or amount of pressure (higher or lower) required to produce an optimal image, in dependence upon the information received from the various sensor devices 54, 56, 58, 60. In this respect, the feedback device informs the patient when compression rate and/or pressure applied is sufficient to obtain a quality image, as determined from a blood pressure or other measurement taken from the patient through sensing devices 54, 56, 58, or 60, before or during the compression and/or clamping phase.

Figure 5:
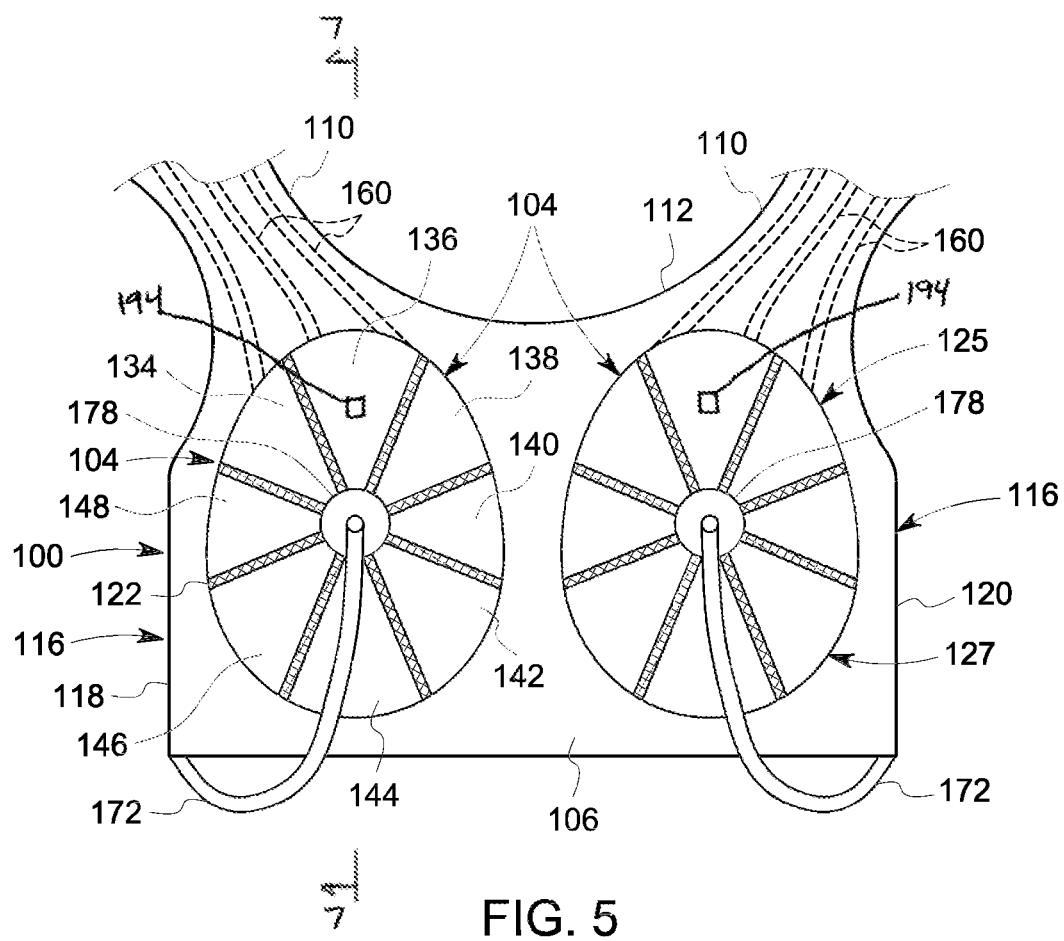
FIG. 5 is a front elevation view of a mammography compression brassiere employed in conjunction with the system of FIG. 3, in accordance with an embodiment of the disclosure.
Figure 6:
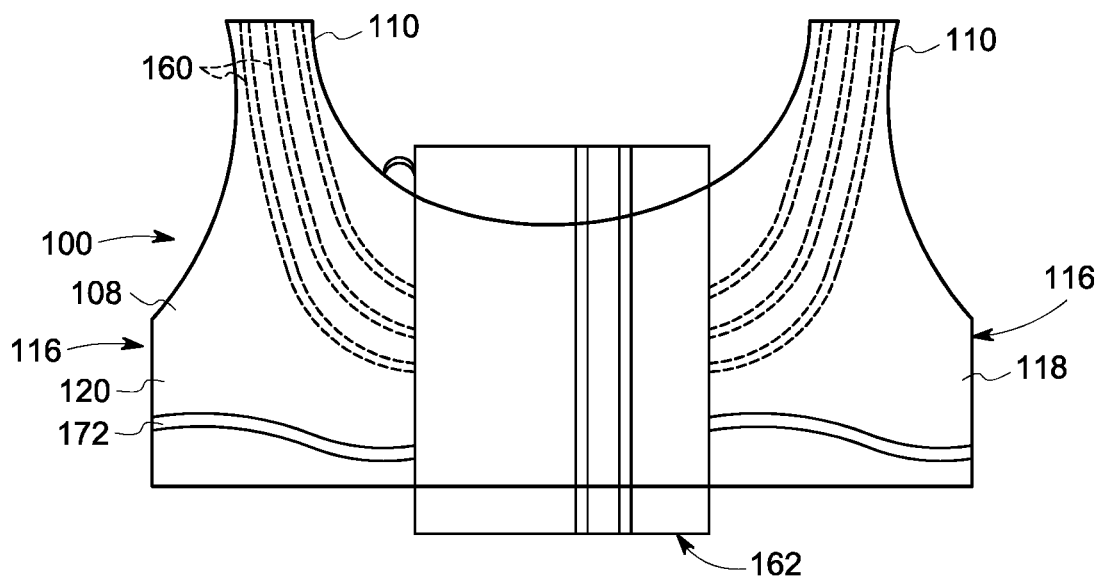
FIG. 6 is a rear elevation view of the brassiere of FIG. 5.

Referring now to FIGS. 5 and 6, an exemplary illustrated embodiment of a brassiere 100 is disclosed for use with the imaging system 10. The brassiere 100 is formed to provide support to the breasts 102 of the patient being imaged in a manner similar to that of existing brassieres, and includes a body 104 including a front portion 106 and a rear portion 108 that are joined, optionally releasably, to one another by a number of shoulder straps 110 extending between the upper ends 112, 114 of the front portion 106 and rear portion 108, and/or side walls 116 extending between adjacent side ends 118, 120 of the front portion 106 and rear portion 108, respectively. The body 104 of the brassiere 100 is formed from a suitable radiolucent material, such that x-ray emitted from the radiation source 16 can pass unhindered through the body 104 and into the breast 102, where the x-rays are absorbed/attenuated in part by the tissue within breast 102 prior to contacting the detector 18 to provide the image data to enable the imaging system 10 to form the x-ray images of the interior structure of the breast 102.

The front portion 106 of the body 104 incudes a pair of apertures 122 within which the breasts 102 of the patient are positioned. The apertures 122 can have different shapes and/or sizes in order to accommodate varying sizes of the breasts 102 of a particular patient. The front surface 106 also includes a pair of cups 124 secured to the front surface 106 around the periphery of and extending over the apertures 122. The cups 124 vary in size according to the size of the apertures 122 in to accommodate variations in the size of the breasts 102 of the patient. In an alternative embodiment, the body 104 can be formed with only a single aperture 122 and associated cup 124.

Figure 7:
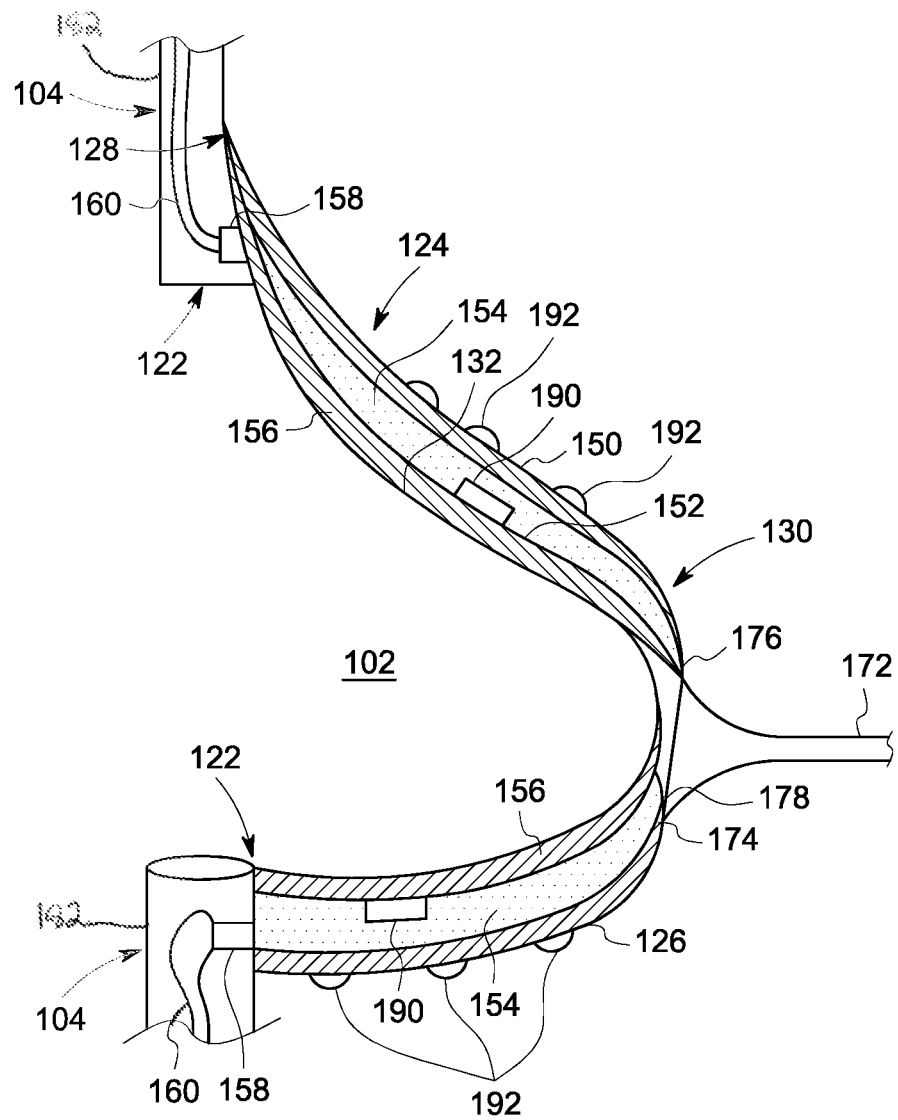
FIG. 7 is a cross-sectional view along line 7-7 of FIG. 5.

Looking now at FIGS. 5 and 7, each cup 124 is formed of an outer layer 126 including a dome shape with a wide end 128 and a narrow end 130 in order to accommodate the breast 102 therein. The outer layer 126 is formed of a radiolucent material and has the wide end 128 secured to the front portion 106 around the aperture 122 in any suitable manner, such as by utilizing an adhesive, stitching, or any other suitable fixed or releasable connection mechanism.

The outer layer 126 defines an interior 132 between the wide end 128 and the narrow end 130 within which are positioned a number of inflatable chambers 134,136,138, 140,142,144,146,148. The number of chambers 134-148 present within the interior 132 can vary as necessary, but in the illustrated exemplary embodiment the brassiere 100 includes eight (8) chambers 134-148. The illustrated exemplary embodiment in FIG. 6 also shows each chamber 134-148 as being formed with the same dimensions to be disposed over an equal portion of the interior 132, however the chambers 134-148 can be formed to have unequal configurations in order to provide different functionality to the brassiere 100, in a manner to be described. Also, the chambers 134-148 can be disposed on only a portion of the cup 124, such as only on an upper half 125 of the cup 124, with the lower half 127 including only the cushion/cushion material 156, to be described, or vice versa.

The chambers 134-148 each include an outer surface 150 disposed against and secured to the outer layer 126 in a suitable fixed or releasable manner, such as by an adhesive or mechanical mechanism, and an inner surface 152 shaped complementary to the outer surface 150 and secured in an airtight manner to or adjacent to the perimeter of the outer surface 150 to define an inflatable pocket 154 therebetween. In an alternative embodiment, the outer surface 150 can be omitted and the inner surface 152 can be secured directly to the outer layer 126 in order to form the pocket 154 and associated chamber 134-148. In this alternative embodiment, the inner surface 152 of each chamber 134-148 can be formed as a single piece of material that is secured to the outer layer 126 to separate portions of the inner surface 152 from one another in order to form the pockets 154. In still another alternative embodiment, the outer surface 150 can include a cushion (not shown) between the outer surface 150 and the outer layer 126 to provide further comfort to the breast 102 positioned within the cup 124.

Opposite the pocket 154, the inner surface 152 includes a cushion material 156, such as a cushion formed of a radiolucent foam material, that can directly contact the breast 102 to provide a comfortable surface for the breast 102 in engagement with the cup 124. Each of the materials forming the chambers 134-148 and the cushion material 156 is radiolucent, such that the chambers 134-148 do not interfere with the transmission of x-rays from the radiation source 16 through the breast 102 and into contact with the detector 18. In an alternative exemplary embodiment, the cushion/cushion material 156 can be formed of a single piece of material that is secured to the inner surface 152 in a suitable manner, such as by using the same connections employed to secure the inner surface 152 to the outer surface 150 and/or outer layer 126. By using a single piece of material for the cushion 156, the engagement between the cushion 156 and the breast 102 can be improved to hold the cup 124 in position against the breast 102.

Each chamber 134-148 additionally includes a port 158 extending through at least one of the outer surface 150 or the inner surface 152 in communication with the pocket 154. Each port 158 is operably connected to an air tube 160 that extends outwardly from the port 158 on the particular chamber 134-148. The tubes 160 in the illustrated exemplary embodiment of FIGS. 5 and 6, are routed from the ports 158 through an inner space 163 defined between layers (not shown) forming each of the front portion 106 and rear portion 108 of the body 104 to maintain the air tubes 160 in connection with the ports 158 and in a location where the air tubes 160 do not become entangled with objects on or adjacent the exterior of the body 104.

Figure 8:
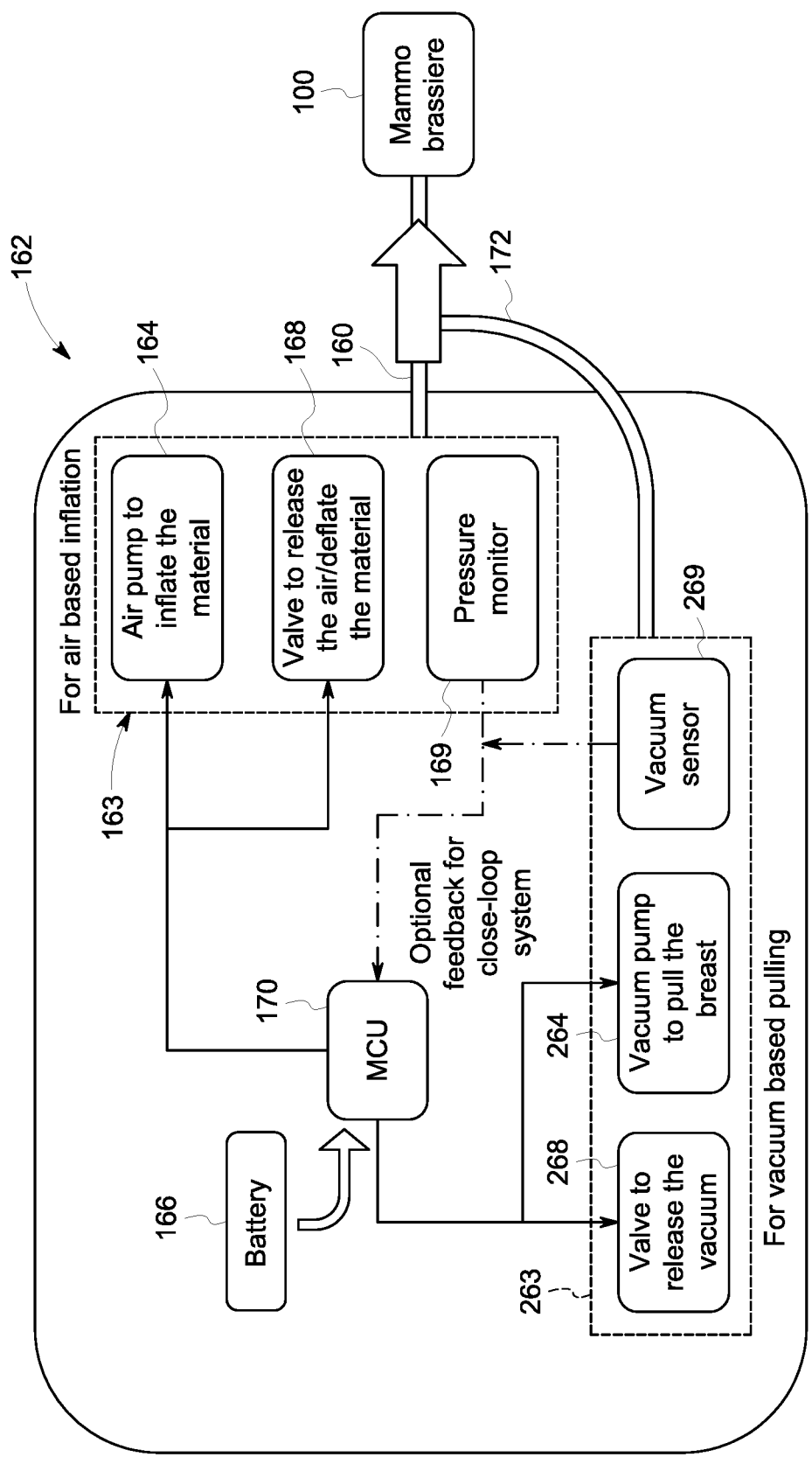
FIG. 8 is schematic diagram of an inflation control module employed with the brassiere of FIG. 5 in accordance with an embodiment of the disclosure.

Further, opposite the ports 158, the air tubes 160 are interconnected with an inflation module 162 disposed on the rear portion 108 of the body 104. As shown in the illustrated exemplary embodiment of FIGS. 6 and 8, the inflation module 162 includes an inflation system 163, a vacuum system 263 and an optionally rechargeable battery/power source 166 connected to each of the inflation system 163 and the vacuum system 263, though the module 162 can alternatively include either of the inflation system 163 or the vacuum system 263 in other embodiments.

The inflation system 163 includes an air pump 164, a release valve 168 operably connected to the pump 166 to vent air from the chambers 134-148, and a pressure monitor 169 operable to measure and provide information on the pressure exerted by any one or more of the chambers 134-148. The vacuum system 263 includes a vacuum pump 264, a release valve 268 operably connected to the pump 264 to withdraw air from the space 176 (FIG. 7), and a pressure monitor 269 operable to measure and provide information on the vacuum exerted on the space 176. The inflation module 162 additionally includes a control mechanism 170 operably connected to power source 166, the inflation system 163, e.g., the air pump 164 and the release valve 168, and to the vacuum system 263, e.g., the vacuum pump 264 ad the release valve 268, to control the inflation and deflation of the chambers 134-148 collectively, individually or in any combination thereof and the vacuum formed within the space 176 The control mechanism 170 can include controls on the rear surface 106 for operation by a technician performing the imaging procedure, and/or can be operably connected through a wired or wireless connection to the imaging system 10, which can remotely operate the inflation module 170 through control signals sent from the controller 32. Further, the pressure monitors 169,269 can be operably connected to the control mechanism 170 to provide feedback to the control mechanism 170 for a closed loop operation of one or both of the inflation system 163 and the vacuum system 263.

The air tubes 160 can be fixed or releasably engaged with the inflation system 163 of the inflation module 162, such that the inflation module 162 can be releasably engaged with the body 104 for use, and then disengaged in order to enable the body 104 to be cleaned or disposed of after use, while allowing the inflation module 162 to be re-engaged with the cleaned body 104 or a new body 104 for additional uses. The inflation module 162 can be held on the rear portion 108 of the body 104 in any suitable manner, such as by one or more releasable mechanical fasteners, e.g., snaps, zipper, or hook and loop fasteners, among others.

Looking now at FIGS. 4-6, the cup 124 additionally includes a vacuum tube 172 attached over an opening 174 located at the narrow end 130 of the cup 124. The vacuum tube 172 extends from the narrow end 130 around the exterior of the body 104 into connection with the vacuum system 263 of the inflation module 162. The connection of the vacuum tube 172 with the vacuum system 263, which can be similar in construction to the connection between the air tubes 160 and the inflation system 163, enables the pump 264 to draw air out of the space 176 defined between the breast 102 and the narrow end 130 when the breast 102 is disposed within the interior 132 of the cup 124 in engagement with the cushion(s) 156. The engagement of the vacuum tube 172 around the opening 174 and the positioning of the breast 102 against the cushion 156 seals the space 176 sufficiently to enable the vacuum system 263 to create a vacuum within the space 176 by drawing air from the space 176 through the vacuum tube 172. In an alternative embodiment, in order to more effectively seal the vacuum tube 172 with the opening 174, the vacuum tube 172 can include a circular flange 178 disposed on the vacuum tube 172 that is positioned within the space 176 and sealed around the opening 174.

Figure 9:
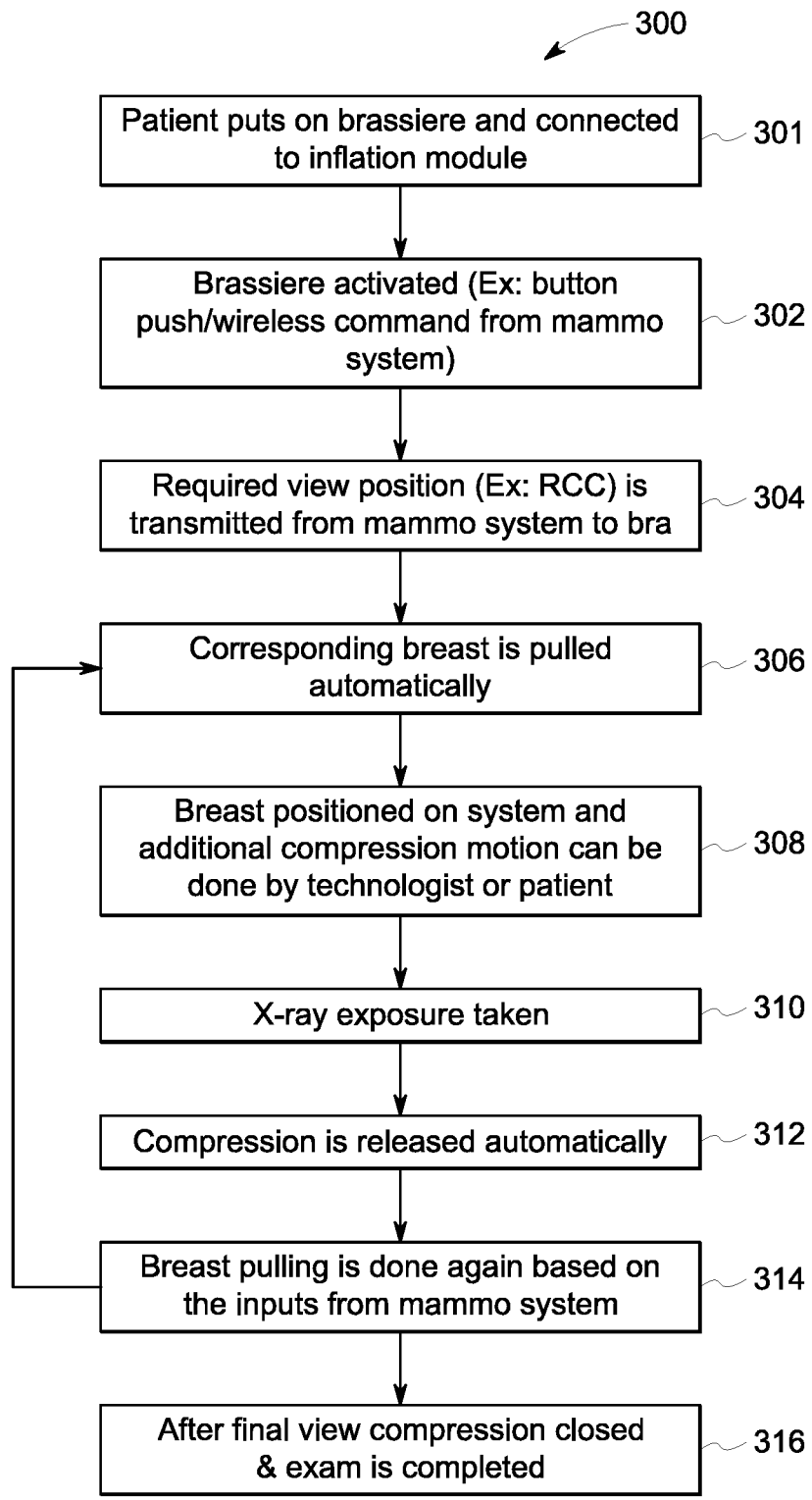
FIG. 9 is flowchart of the method of compression and imaging of a breast performed by the brassiere and imaging system of FIGS. 3 and 5 in accordance with an embodiment of the disclosure.
Figure 11:
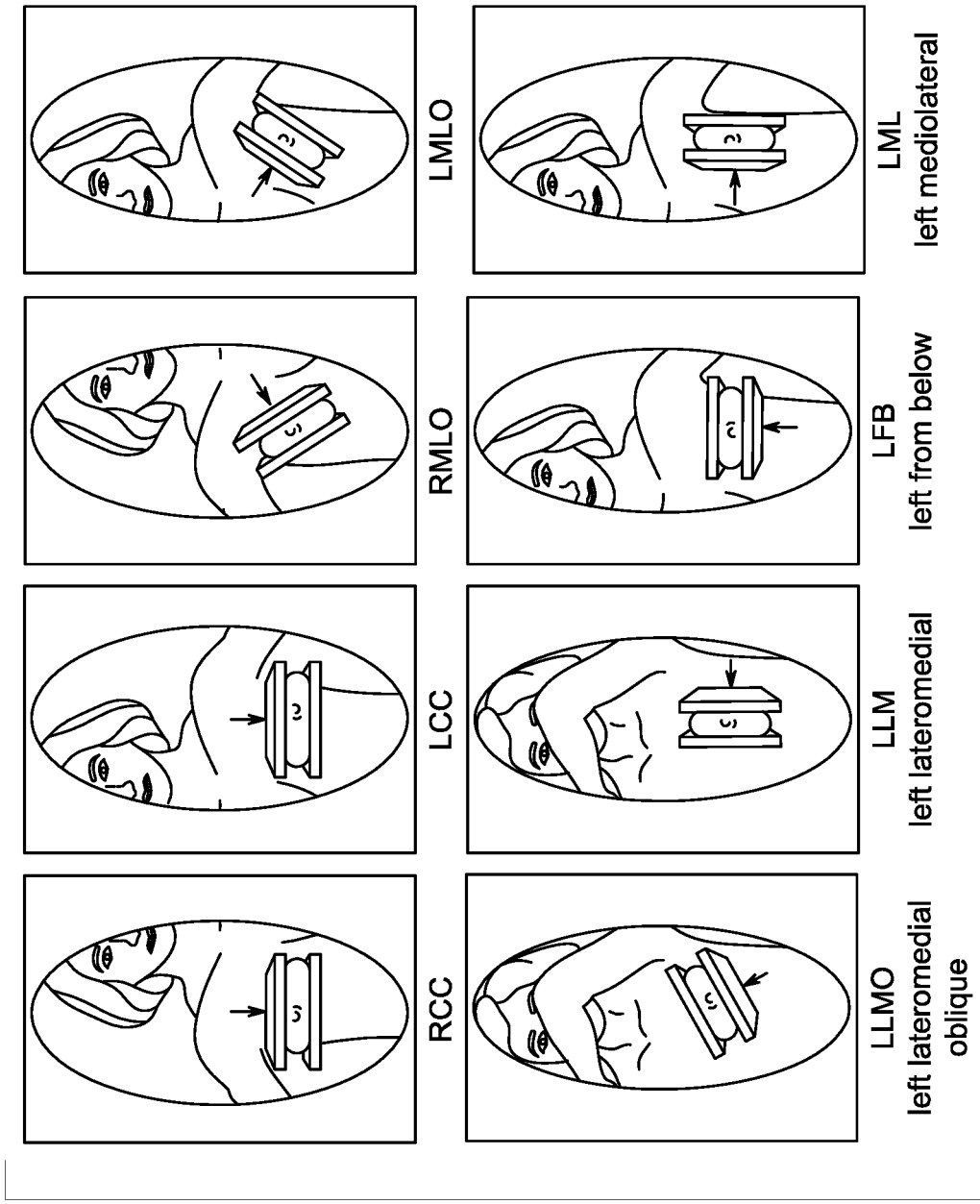
FIG. 11 is a schematic representation of compressed breast positions in standard mammography image views to be obtained by the brassiere and imaging system of FIGS. 3 and 5 in accordance with an embodiment of the disclosure.

Referring now to FIGS. 9-11, in an exemplary embodiment of a method 300 of operation, initially in step 301 the patient puts on the brassiere 100 to position the breast 102 within the cups 124 (FIG. 10A) and any necessary connections between the brassiere 100, the tubes 160,172 and the inflation module 162 are made. In step 302, the technician activates the inflation module 162 either manually on the module 162 or via a remote command from the imaging system 10. In step 304, depending upon the desired view of the breast 102 to be imaged by the system 10, the system 10 transmits information concerning the image view to be taken to the inflation module 162. In step 306, the inflation module 162 operates the pump 164 of the inflation system 163 to inflate one or more of the chambers 134-148 in a manner that compresses the breast 102 and/or the pump 264 of the vacuum system 263 to pull the breast 102 forward to conform the breast 102 at least generally to the desired compressed shape for the specified image view (FIG. 10B).

Depending on the various standard mammography views (CC/LMO/MLO/FB/LM/ML; see FIG. 11), different breast tissue regions need to be compressed by the cups 124. As a result, different air chambers 134-148 can be inflated based on the view input from mammography system 10. For example, if the desired view is the right breast craniocaudal view (RCC), chambers 134,136,138,142,144 & 146 can be inflated in the cup 124 containing the right breast 102 for imaging. Additionally, if the desired or next view is the left breast mediolateral view (LML), chambers 134,138,140, 142, 146, and 148 can be inflated in the cup 124 containing the left breast 102 Further, if the desired or next view is the left breast lateral mediolateral oblique view (LMLO), chambers 134,136,140,142,144 and 148 can be inflated of the cup 124 containing the left breast 102. For each desired configuration for the elected image view, the number of chambers 134-148 that are inflated and to what extent they are inflated, as the chambers 134-148 can be inflated independently of one another and/or to varying pressures, can vary depending upon the breast size and selection of activation chambers can be customized. The chambers 134-148 are positioned to cover the pectoralis muscle and other axillary tissue as well for proper compression for imaging purposes.

As the chambers 134-148 are inflated by the pump 164 of the inflation system 163 and the vacuum pump 264 draws the breast 102 forward in the cup 124, the chambers 134-148 and cushion 156 reduces the pain and/or discomfort associated with the compression. In one embodiment, the compression of the breast 102 starts with gradual inflation of the chambers 134-148 and the subsequent combination of inflation of the chambers 134-148 vacuum pulling via the tube 172 to pull the nipple region forward, which results in positioning the breast 102 appropriately for the desired image. As such, the inflatable chambers 134-148 help to shape the breast 102 depending on the view needed and helps to avoid the tissue overlap and/or wrinkling. Further, any one or more of the chambers 134-148 can also have multiple compartments (not shown) to assist in gradually increasing the pressure within the particular chamber 134-148.

Upon reaching the desired configuration, in step 308 the breast 102 compressed within the brassiere 100 is positioned on the detector 18 of the system 10 and engaged by the compression paddle/plate 28 to apply any further required compression for the desired imaging view to be obtained (FIG. 10C). In performing the additional compression with the paddle 28, the chambers 134-148 and/or cushion 156 operate to continue to lessen any pain or discomfort associated with the compression by the paddle 28.

After the image is taken by the system 10 in step 310, in step 312 the paddle 28 is moved away from the breast 102 and the inflation module 162 operates either or both of the release valves 168,268 in inflation system 163 and vacuum system 263 to release the pressure exerted on the breast 102 via the chambers 134-148 and/or the vacuum tube 172. In step 314, a configuration for the compression of the breast 102 for a subsequent view, such as any of the views illustrated in FIG. 11, is transmitted to the inflation module 162, and the module 162 returns to step 306 to reconfigure the breast 102 within the cup 124 using the chambers 134-148 and the vacuum tube 172 in an arrangement corresponding to the desired compression of the breast 102. The steps 308-310 are again performed to obtain the desired view. After completion of each desired image view, in step 316 the module 162 again operates the release valves 168,268 to remove the compression on the breast 102 and the patient can remove the brassiere 100.

Referring now to the illustrated exemplary embodiments of FIGS. 12 and 13, in the situation where the imaging system 10 additionally includes the biopsy system 98, the cups 124 of the brassiere 100 can be configured to include removable chambers 134-148. In these embodiments, the chambers 134-148 are formed as self-contained chambers 134-148, each having radiolucent attachment devices 180, e.g., hook and loop closures (FIG. 12) or snaps (FIG. 13), among other suitable closures, located on opposed sides of the chambers 134-148 and releasably engageable with complementary devices 180 on adjacent chambers 134-148 in order to form the chambers 134-148 in the cups 124. Thus, when it is desired to perform a biopsy procedure on a region or area of interest (ROI) illustrated within the images of the breast 102 disposed within the brassiere 100 of FIG. 12 or FIG. 13, the individual chamber 134-148 covering the ROI within the breast 102 to be biopsied can be removed from the cup 124, thereby exposing the area breast 102 containing the ROI to allow access to the ROI by the biopsy system 98. Further, as the chambers 134-148 are separate from one another, the compression provided by the remaining chambers 134-148 can be maintained during the biopsy procedure to assist in maintaining the desired position of the breast 102 on the system 10.

Figure 14:
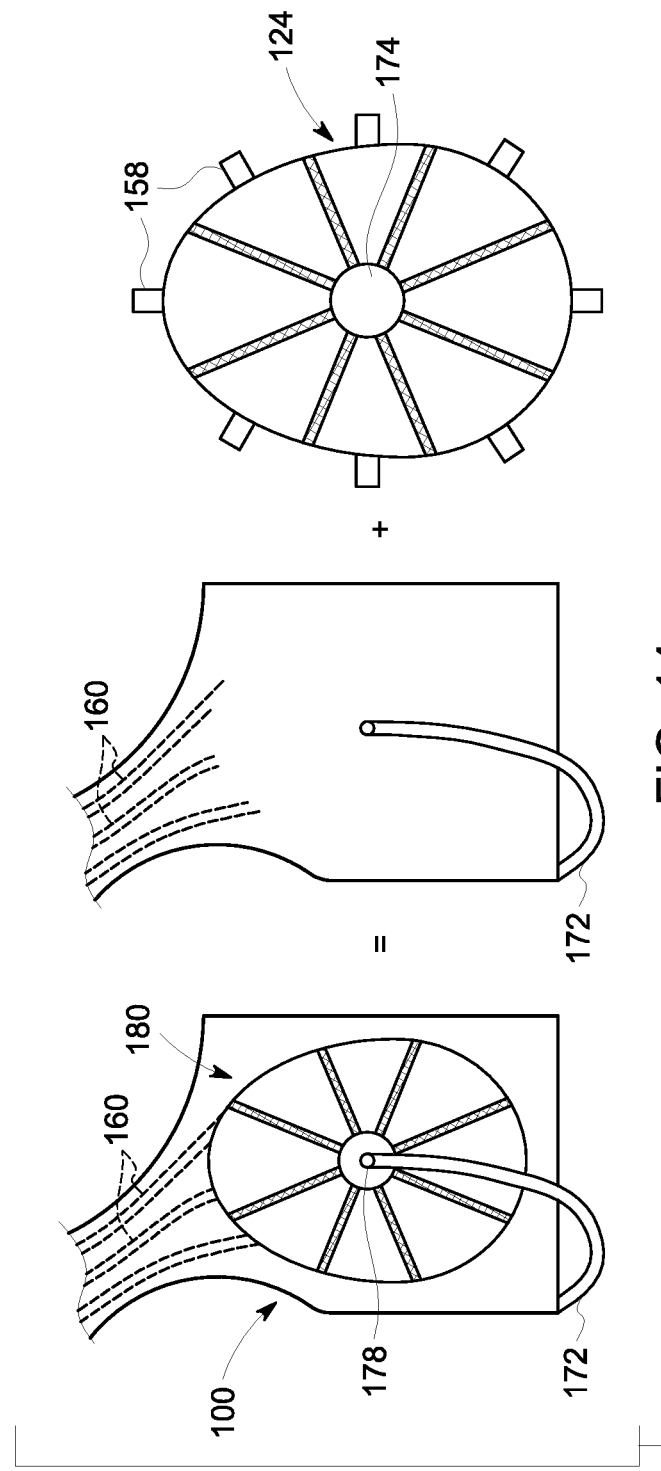
FIG. 14 are isometric views of another embodiment of the brassiere of FIG. 5, including a separable cup in accordance with another embodiment of the disclosure.

Looking now at the illustrated exemplary embodiment of FIG. 14, to minimize any sanitary issued with the use of the brassiere 100, the cups 124 can be formed to be removable from the body 104. The cups 124 can be disconnected from the air tube 160 and the vacuum tube 172 such that the cups 124 can be sanitized or disposed of after use. This also increases the ease of cleaning the brassiere 100, as the body 104 can be cleaned separately with or without the inflation module 162 connected to the body 104.

Figure 15:
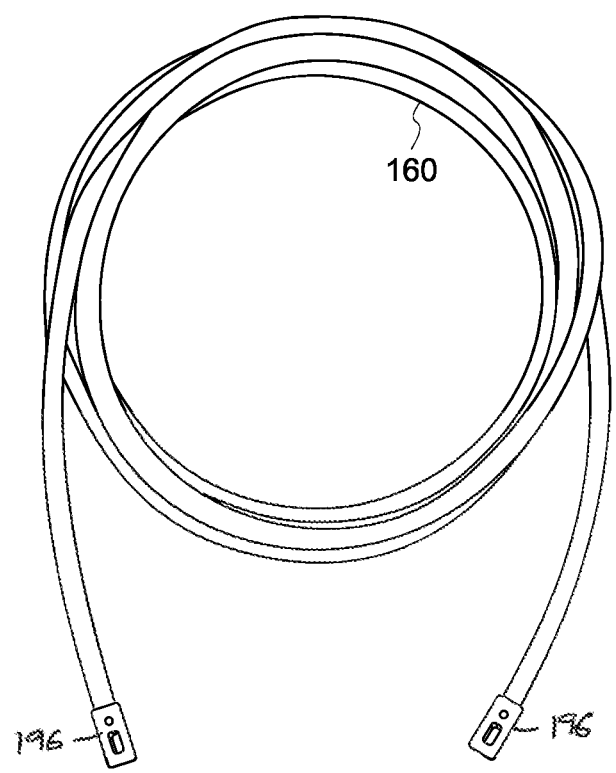
FIG. 15 is an isometric view of a removable air tube utilized in the brassiere of FIG. 5.

Further, as shown in the exemplary illustrated embodiment of FIGS. 5 and 15, the air tubes 160 can be retained within sleeves 182 formed within the interior of the body 104. The sleeves 182 are formed of the same or similar radiolucent materials as used for the body 104 and operated to control and/or route the air tubes 160 through the body 104. For cleaning purposes, the air tubes 160 can be removed from within the sleeves 182, such as by disengaging connectors 196 on the ends of the tube 160 from the ports 158, allowing the body 104 to be cleaned and reused with another patient separately from the air tubes 160, which may either be cleaned and reinserted within the sleeves 182 to reconnect the connectors 196 with the ports 158, optionally in conjunction with the removeable cups 124 in the embodiment of FIG. 14, or discarded and replaced.

In other exemplary embodiment of the disclosure, radiolucent pressure sensors 190 can be incorporated inside the brassiere 100 from which force values can be calculated. The pressure sensors 190 are operably connected to the inflation module 162 such that the inflation/pressure being exerted on the breast through the chambers 134-148 and/or vacuum tube 172 can be stopped once it reaches a predetermined threshold and/or once the gradient pressure change is negligible with inflation. If any additional compression of the breast 102 is needed, that compression can be applied via the paddle 28.

In still another exemplary embodiment of the disclosure, due to the presence of the cushion/foam 156, thickness measurements currently employed in mammography systems 10, such as thickness measurement obtained by a potentiometer or encoder, are not effective as they cannot differentiate the thickness of the compressed cushion material 156 thickness from the thickness of the actual breast 102. Because an accurate thickness measurement for the breast 102 is desired for a variety of purposes, including the calculation of optimal imaging parameters for the breast 102, the system 10 employing the brassiere 100 can obtain an accurate thickness measurement in other suitable manners and/or processes, such as by: 1. obtaining stereoscopic images to calculate the compressed breast depth/thickness; 2. using the controller 32 to subtract the offset thickness, i.e., the compression of cushion material 156 without the breast 102 as calculated or estimated empirically beforehand for each brassiere 100 or cup 124, from the overall thickness measured after compression of the cup 124 with the breast 102; or 3. employing an artificial intelligence/machine learning-based automatic thickness calculation from the calculated distance between the paddle 28 and the detector 18, the brassier size, and the amount of air pressure/vacuum level applied during compression of the breast 102 within the brassiere 100, among other suitable methods.

In still another exemplary embodiment of the disclosure, the brassiere 100 can have radiolucent markings 192 (FIG. 5) on it to help with aligning the breast 102 on the detector 18 using associated markings on the detector 18, light beams illuminating the proper position on the detector 18 for alignment with the markings on the brassier 100, augmented reality (AR) marking/positioning systems, or similar technology. These markings will enable the patient/technologist to properly locate the brassiere 100 and breast 102 therein on the detector 18 to expose complete breast tissue for imaging by the system 10.

The brassier 100 can additionally include various components disposed on the outer layer 126 to assist in holding the brassier 100 in the desired position between the paddle 28 and the detector 18. More specifically, in FIG. 7 an exemplary embodiment the outer layer 126 can include markings, dots and/or strips 192 of a high friction material, e.g., a silicon rubber, disposed thereon. The strips 192 act to provide enhanced friction or grip between he outer layer 126 and the paddle 28 and detector 18 to assist in holding the outer layer 126, and breast 102 contained therein where desired between the paddle 28 and the detector 18.

Finally, it is also to be understood that the system 10 may include the necessary electronics, software, memory, storage, databases, firmware, logic/state machines, microprocessors, communication links, displays or other visual or audio user interfaces, printing devices, and any other input/output interfaces to perform the functions described herein and/or to achieve the results described herein. For example, as previously mentioned, the system may include at least one processor and system memory/data storage structures, which may include random access memory (RAM) and read-only memory (ROM). The at least one processor of the system 10 may include one or more conventional microprocessors and one or more supplementary co-processors such as math co-processors or the like. The data storage structures discussed herein may include an appropriate combination of magnetic, optical and/or semiconductor memory, and may include, for example, RAM, ROM, flash drive, an optical disc such as a compact disc and/or a hard disk or drive.

Additionally, a software application that adapts the controller to perform the methods disclosed herein may be read into a main memory of the at least one processor from a computer-readable medium. The term "computer-readable medium", as used herein, refers to any medium that provides or participates in providing instructions to the at least one processor of the system 10 (or any other processor of a device described herein) for execution. Such a medium may take many forms, including but not limited to, non-volatile media and volatile media. Non-volatile media include, for example, optical, magnetic, or opto-magnetic disks, such as memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, a RAM, a PROM, an EPROM or EEPROM (electronically erasable programmable read-only memory), a FLASH-EEPROM, any other memory chip or cartridge, or any other medium from which a computer can read.

While in embodiments, the execution of sequences of instructions in the software application causes at least one processor to perform the methods/processes described herein, hard-wired circuitry may be used in place of, or in combination with, software instructions for implementation of the methods/processes of the present invention. Therefore, embodiments of the present invention are not limited to any specific combination of hardware and/or software.

It is understood that the aforementioned compositions, apparatuses and methods of this disclosure are not limited to the particular embodiments and methodology, as these may vary. It is also understood that the terminology used herein is for the purpose of describing particular exemplary embodiments only, and is not intended to limit the scope of the present disclosure which will be limited only by the appended claims.

We claim:

1. A brassiere comprising:
   a. a body including at least one aperture formed therein;
   b. a cup secured to the body around the aperture, the cup including at least one inflatable chamber and at least one cushion disposed on a breast contact surface of the cup; and
   c. an inflation module operably connected to the at least one inflatable chamber to selectively inflate and deflate the at least one inflatable chamber.

2. The brassiere of claim 1, wherein the cup is releasably secured to the body.

3. The brassiere of claim 1, wherein the at least one cushion is disposed on a breast contact surface of the at least one inflatable chamber.

4. The brassiere of claim 1, wherein the cup includes a wide end secured to the body and a narrow end opposite the wide end that define and interior therebetween, wherein the narrow end includes an opening therein and further comprising a vacuum tube connected to the narrow end around the opening.

5. The brassiere of claim 4, wherein the inflation module comprises:
   a. an inflation system operably connected to the at least one inflation chamber;
   b. a vacuum system operably connected to the vacuum tube;
   c. a control mechanism operably connected to the inflation system and to the vacuum system; and
   d. a power source operably connected to each of the inflation system, the vacuum system and the control mechanism.

6. The brassiere of claim 5, wherein the inflation system and the vacuum system each comprise:
   a. a pump;
   b. a release valve; and
   c. a pressure sensor.

7. The brassiere of claim 5, wherein the control mechanism is adapted to be operably connected with at least one of a wired or wireless connection to a controller of a mammography imaging device.

8. The brassiere of claim 1, wherein the inflation module is releasably attached to the body and to the at least one inflatable chamber.

9. The brassiere of claim 1, wherein the cup includes a number of inflatable chambers disposed along one of a lower half or an upper half of the cup.

10. The brassiere of claim 1, wherein the at least one inflatable chamber comprises:
    a. an outer surface;
    b. an inner surface connected to the outer surface to define a pocket therebetween; and
    c. an air tube operably connected between the pocket and the inflation module.

11. The brassiere of claim 1, wherein the at least one inflatable chamber comprises:
    a. an outer surface;
    b. an inner surface connected to the outer surface to define a number of individual inflatable chambers having pockets formed therein; and
    c. a number of air tubes, each air tube operably connected between one of the number of inflatable chambers and the inflation module.

12. The brassiere of claim 11, wherein the number of inflatable chambers are releasably secured to the cup body and to one another.

13. A method for compressing a breast into a desired shape for a mammography imaging procedure on an imaging device, the method comprising the steps of:
    a. providing a brassiere comprising:
       i. a body including at least one aperture formed therein;
       ii. a cup secured to the body around the aperture, the cup including at least one inflatable chamber and at least one cushion disposed on a breast contact surface of the cup; and
       iii. an inflation module operably connected to the at least one inflatable chamber to selectively inflate and deflate the at least one inflatable chamber;
    b. positioning the breast within the cup;
    c. inflating the at least one inflatable chamber to compress the breast within the cup; and
    d. placing the brassiere and the breast compressed therein on the imaging device to perform the mammography imaging procedure.

14. The method of claim 13, wherein the cup includes a number of inflatable chambers disposed within an interior of the cup, and wherein the step of inflating the at least one inflatable chamber comprises selectively inflating each of the number of inflatable chambers to compress the breast.

15. The method of claim 13, wherein the cup includes a wide end secured to the body, a narrow end opposite the wide end, and a vacuum tube connected to an opening in the narrow end; and wherein the method further comprises the step of applying a vacuum to the narrow end through the opening.

16. The method of claim 13, wherein the inflation module includes a control mechanism operably connected to the inflation system, and wherein the step of inflating the at least one inflatable chamber to compress the breast is performed by automatically by the control mechanism.

17. The method of claim 16, wherein the imaging device is a mammography imaging device including a controller including data concerning a breast position for obtaining at least one image of the breast with the mammography imaging device, the method further comprising the steps of
    a. transmitting the data concerning the breast position from the controller of the mammography imaging device to the control mechanism of the inflation module; and
    b. inflating the at least one inflatable chamber to compress the breast into the breast position.

18. The method of claim 17, wherein the mammography imaging system includes a compression plate movable with respect to a detector, and wherein the step of placing the brassiere and the breast compressed therein on the imaging device to perform the mammography imaging procedure comprises the steps of:
    a. positioning the brassiere and compressed breast therein on the detector after inflating the at least one inflatable chamber to compress the breast into the breast position; and
    b. moving the compression plate to further compress the breast.

19. A mammography system comprising:
    a. a mammography imaging device including:
       i. a gantry including a radiation source, a detector alignable with the radiation source, and a compression paddle moveable relative to the detector to secure a patient breast therebetween; and ii. a controller operably connected to the gantry to control the operation of the radiation source and detector to generate image data, and to control the operation of the biopsy device in an interventional/biopsy mode for the mammography system, the controller including a central processing unit and interconnected database for processing the image data from the detector, a display operably connected to the controller for presenting information to a user, and a user interface operably connected to the controller to enable user input to the controller; and b. a brassiere operably connected to the controller and adapted to compress a breast into a desired position prior to placement of the breast on the detector, the brassier comprising:

i. a body including at least one aperture formed therein;

ii. a cup secured to the body around the aperture, the cup including at least one inflatable chamber and at least one cushion disposed on a contact surface of the cup; and iii. an inflation module operably connected to the at least one inflatable chamber to selectively inflate and deflate the at least one inflatable chamber.

20. The mammography system of claim 19, wherein the inflation module includes a control mechanism operably connected to the controller and configured to selectively inflate and deflate the at least one inflatable chamber in response to data concerning a breast position for obtaining at least one image of the breast transmitted from the controller to the control mechanism.

* * * * *